United States Patent [19]

Guzowski

[11] 4,309,774

[45] Jan. 12, 1982

[54] VENTILATING HELMET

[76] Inventor: Chester D. Guzowski, 291 Sequoia Ct., #11, Thousand Oaks, Calif. 91360

[21] Appl. No.: 182,962

[22] Filed: Sep. 2, 1980

Related U.S. Application Data

[63] Continuation-in-part of Ser. No. 50,655, Jun. 21, 1979, abandoned.

[51] Int. Cl.³ .............................................. A61F 9/06
[52] U.S. Cl. ............................................ 2/8; 2/171.3
[58] Field of Search ...................... 2/8, 9, 171.3, 206, 2/422

[56] References Cited

U.S. PATENT DOCUMENTS

| 3,238,535 | 3/1966 | Richey | 2/8 |
| 3,629,868 | 12/1971 | Greenlee | 2/8 |
| 3,943,573 | 3/1976 | Budmiger | 2/8 |
| 4,150,443 | 4/1979 | McNeilly | 2/171.3 X |

Primary Examiner—Peter P. Nerbun
Attorney, Agent, or Firm—Jack C. Munro

[57] ABSTRACT

A ventilating helmet which takes the form of sheet material wall member which has mounted thereon an electrically operated fan which is adapted to move air to the interior of the helmet. The electrically operated fan is to be operated through the use of a light sensitive, electrical energy producing cell. This cell is to be directly exposed to the source of light energy.

3 Claims, 2 Drawing Figures

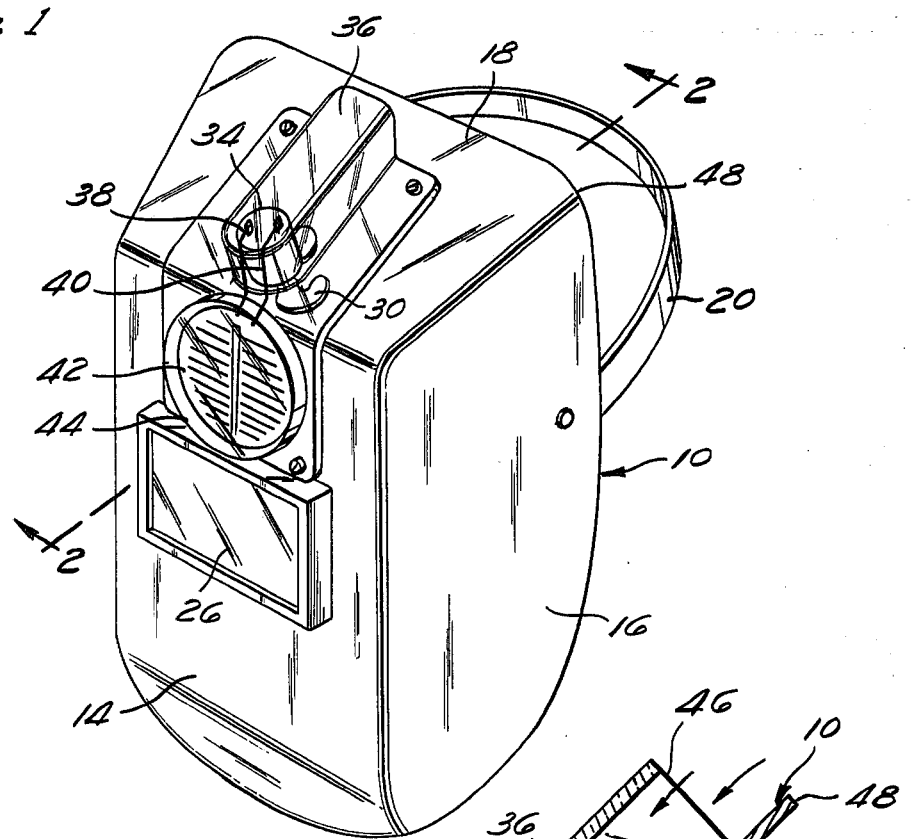
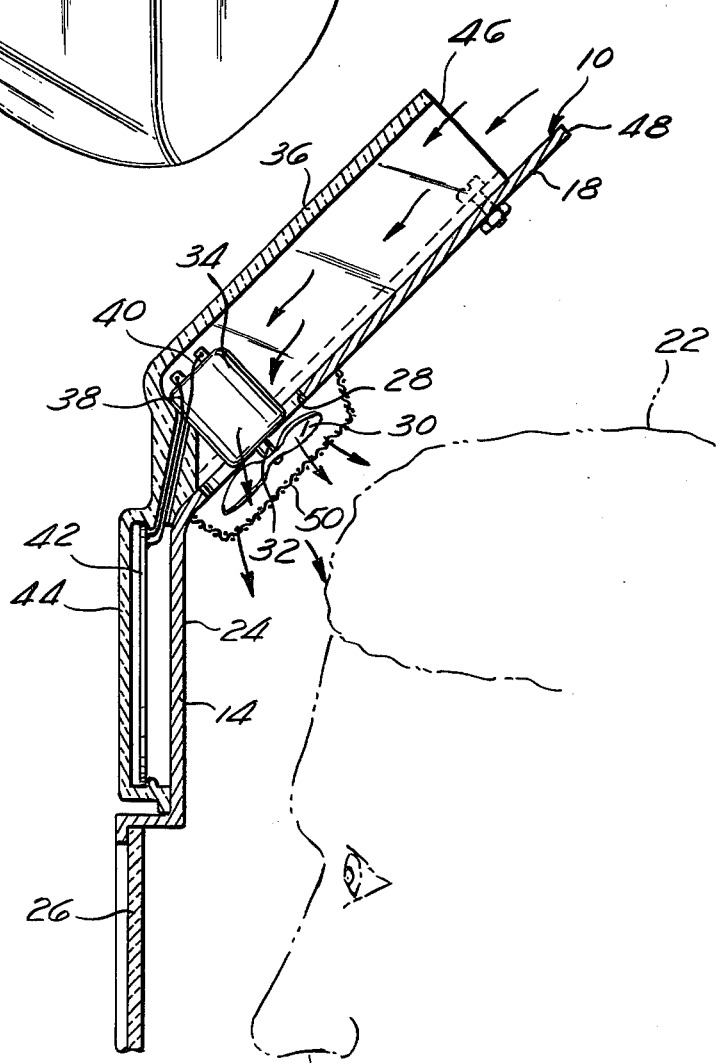

VENTILATING HELMET

REFERENCE TO PRIOR APPLICATION

This application is a continuation-in-part application of U.S. patent application Ser. No. 50,655, filed June 21, 1979, (now abandoned) by the present inventor.

BACKGROUND OF THE INVENTION

This invention relates to helmets and more particularly to a helmet which includes a fan device in order to move air onto the wearer's face to deter perspiring of the wearer.

One of the uses of the present invention is in relation to a welding helmet. The use of welding helmets during the performing of welding is well known. Such welding helmets include a darkened window glass in the front surface thereof through which the operator is to observe the welding area in order to prevent damage to the operator's eyes due to the high intensity of the welding arc.

This welding arc also creates a high level of heat. This heat has a tendency to cause the operator to perspire, especially if the operator is located in an enclosed environment. The welding helmet itself, because it encloses the operator's head, further adds to the tendency to perspire. Needless to say, it is quite annoying to the operator, who is trying to produce a strong weld, to be hindered by droplets of perspiration which fall into the operator's eyes.

Previously, there have been efforts at designing ventilated welding helmets. However, these welding helmets normally include a complex structure of a fan which is operated through an electrical battery source, such as a conventional electrical storage battery. The operation of the ventilation means is solely through the use of a manually operated switch. Welding is normally a sporadic procedure and does not occur continuously. Therefore, each time the operator momentarily stops the welding procedure and removes his helmet, it is required that the operator manually disengage the ventilating fan. When the operator decides to continue with the welding, the operator is again required to reactivate the fan. This continual deactivation and reactivation of the fan ventilation means within the helmet is undesirable.

There is a need for a welding helmet ventilation device which is automatically activated upon initiating of the welding arc and automatically deactivated upon terminating of the welding arc.

Additionally, other types of helmets have poor ventilation, such as outdoor safety helmets (hard hats) for workman. Workman are required to wear such helmets regardless of ambient temperature conditions. As a result, these helmets are quite uncomfortable and excessive perspiration is most common. There is a need for a simple hard hat ventilation device which would automatically cool the wearer's head while the workman is performing required duties in even the most adverse temperature conditions.

SUMMARY OF THE INVENTION

A ventilation device for a helmet, such as a safety helmet, welding helmet, or the like. The ventilation device is to comprise a fan blade operated by an electrical motor. The fan blade and motor are mounted within a sheet material housing. The helmet is to include an opening formed within the helmet wall in a specific desired location. The housing is to be fixedly mounted on the helmet wall and the fan blade is to extend within the opening in the helmet wall. The fan blade is to be electrically driven by a solar cell. The solar cell is to be mounted on the helmet wall and can be connected to the sheet material housing. The solar cell is to produce electricity upon exposure to light energy of sufficient intensity. Sufficient intensity is obtained from normal sunlight or from a welding arc or other similar intensity source of light energy. An air inlet tube is to be attached to the sheet material housing to supply air to the fan blade.

The primary objective of this invention is to construct a helmet ventilation device which operates satisfactorily upon exposure to high intensity light energy.

A further objective of this invention is to construct a helmet ventilation device which is composed of few parts and which is simple in construction facilitating easy installation on a helmet and can be manufactured inexpensively.

BRIEF DESCRIPTION OF THE DRAWING

FIG. 1 is an isometric view of a conventional welding helmet upon which has been mounted the welding helmet ventilation device of this invention; and FIG. 2 is a cross-sectional view taken along line 2—2 of FIG. 1 depicting operation of the ventilation fan incorporated within the welding helmet.

DETAILED DESCRIPTION OF THE SHOWN EMBODIMENT

Although the structure of this invention is described in conjunction with a welding helmet, it is to be understood that this invention can be readily employed on any type of helmet.

Referring particularly to the drawing, there is shown in FIG. 1 a conventional thin sheet material welding helmet 10 which is basically cup-shaped having a front wall 14, side walls 16 (only one being shown) and a top wall 18. The wall member 10 is to be constructed of thin rigid material, such as plastic, metal or fiberglass. A headband 20 connects between the side walls 16 and is adapted to be located about the head of the operator 22. The head of the operator 22 is to be located within the internal chamber 24 formed internally of the wall member 10. Located in the front wall 14 is a darkened window 26. The operator 22 is to observe the welding area through the window 26.

Formed within the top wall 18 is an opening 28. Located adjacent the opening 28 is a fan blade 30. The fan blade 30 is attached to a motor shaft 32. The shaft 32 is to be rotatably driven by an electrically operated motor 34. The motor 34 is fixedly mounted on a tubular extension 36. The tubular extension 36 forms the housing for the motor 34. The tubular extension 36 is fixedly secured by conventional fastening means to the top surface 18.

The motor 34 is electrically connected through electrical conductors 38 and 40 to an electrical energy producing cell 42. This cell 42 is sensitive to light and, upon receiving light energy of a satisfactory level, will cause operation of the motor 34 and operation of the fan blade 30. Such light sensitive cells are well known and referred generally to as silicon solar cells. It is deemed to be part of this invention that more than one cell 42 could be employed.

The solar cell 42 is located within a transparent housing 44 which is fixedly attached to the front surface 14 of the wall member 10. The solar cell 42 is mounted directly adjacent the window 26 and preferably directly above the window 26. Therefore, once the operator has positioned himself to directly observe the welding area, the solar cell 42 is automatically positioned to receive the maximum light energy from the welding area.

The tubular extension 36 terminates in an access opening 46. This access opening 46 is located adjacent the back edge 48 of the wall member 10. The fan blade 30 moves air through the access opening 46 and through the tubular extension 36, through opening 28 and against the operator's face in order to effect dissipation of perspiration. In order to protect the operator's head from the operation of the fan blade 30, a screening material 50 is located about the fan blade 30. This screening material 50 is mounted within the interior chamber 24 on the interior surface of the top surface 18. It is to be noted that the location of the access opening 46 is remote from the front surface 14 so the air that is moved through the tubular extension 13 will not contain any of the noxious gases which may be produced during the welding procedure. In other types of helmets, the tubular extension will be located to draw air generally from the rear area of the helmet to minimize the picking up of foreign material, such as dust.

The operation of the welding helmet ventilation device of this invention is believed to be readily apparent. Once the welding arc is struck, it is observed through the window 26 by the operator 22. The light sensitive cell 42 responds by producing electricity and operates the motor 34 which in turn causes rotation of the fan blade 30. Upon terminating of the welding procedure, the motor 34 is deactivated to again be reactivated upon reinitiation of the welding procedure.

What is claimed is:

1. In combination with a welding helmet, said helmet being formed of a thin sheet material wall member, said wall member having a front surface, said front surface including a window, said helmet including an internal chamber, said internal chamber adapted to receive a person's head with that person being able to observe through said window, the improvement comprising:

an opening formed through said wall member connecting with said internal chamber, a fan blade located within said opening adapted to move air into said internal chamber, said fan blade being electrically operated, an electrical battery source mounted on said front surface of said wall member, said electrical battery source connected to operate said fan blade, said electrical battery source comprising a light sensitive cell, said cell to produce electrical energy to operate said fan blade upon sensing a satisfactory level of light energy such as from a welding arc; and said fan blade being mounted within a housing, said housing including a hollow tubular extension, said extension terminating in an access opening into said ambient, said extension being mounted on the exterior surface of said wall member, said access opening being displaced from said front surface of said wall member and located adjacent the back edges of said wall member, said light sensitive cell being mounted on said housing, whereby said housing can be readily adapted to existing helmet structures with a minimum amount of modification.

2. The combination as defined in claim 1 wherein:

said electrical energy battery source being mounted directly adjacent said window, whereby during a welding operation and the operator looking directly at the welding arc said light sensitive electrical battery source will be positioned in a manner to directly receive maximum light energy from the welding arc.

3. In combination with a helmet, said helmet being formed of a thin sheet material wall member, said wall member having a front and a rear, said front to be positioned directly adjacent the face of the wearer, said rear being spaced from said front, said helmet including an internal chamber, said internal chamber adapted to receive the wearer's head, the improvement comprising:

an opening formed through said wall member connecting with said internal chamber, a fan blade located within said opening adapted to move air into said internal chamber, said fan blade being electrically operated, an electrical battery source mounted on said front surface of said wall member, said electrical battery source connected to operate said fan blade, said electrical battery source comprising a light sensitive cell, said cell to produce electrical energy to operate said fan blade upon sensing a satisfactory level of light energy such as from a welding arc; and said fan blade being mounted within a housing, said housing including a hollow tubular extension, said extension terminating in an access opening into said ambient, said extension being mounted on the exterior surface of said wall member, said access opening being displaced from said front of said wall member and located adjacent said back of said wall member, said light sensitive cell being mounted on said housing, whereby said housing can be readily adapted to existing helmet structures with a minimum amount of modification.

* * * * *